United States Patent [19]

Kolobow

[11] Patent Number: 5,429,127
[45] Date of Patent: Jul. 4, 1995

[54] THIN WALL ENDOTRACHEAL TUBE

[75] Inventor: Theodor Kolobow, Rockville, Md.

[73] Assignee: The United States of America as represented by the Department of Health and Human Services, Washington, D.C.

[21] Appl. No.: 85,948

[22] Filed: Jul. 6, 1993

Related U.S. Application Data

[63] Continuation-in-part of Ser. No. 878,784, May 6, 1992, Pat. No. 5,305,740, which is a continuation-in-part of Ser. No. 758,824, Sep. 12, 1991, abandoned.

[51] Int. Cl.$^6$ ............................................. A61M 16/04
[52] U.S. Cl. ...................... 128/207.14; 128/911; 128/200.26
[58] Field of Search ................. 128/207.14, 207.15, 128/4–8, 911, 204.18, 200.26; 604/281, 280, 282

[56] References Cited

U.S. PATENT DOCUMENTS

| 724,913 | 4/1903 | Montgomery . | |
|---|---|---|---|
| 933,307 | 8/1963 | Kittel . | |
| 3,087,493 | 4/1963 | Schossow | 128/207.15 |
| 3,443,564 | 5/1969 | Oehmig et al. . | |
| 3,659,611 | 5/1972 | Miller | 128/207.15 |
| 3,964,488 | 6/1976 | Ring et al. | 128/207.14 |
| 4,041,936 | 8/1977 | Carden | 128/6 |
| 4,341,210 | 7/1982 | Elam | 128/207.15 |
| 4,665,906 | 5/1987 | Jervis . | |
| 4,795,458 | 1/1989 | Regan . | |
| 4,840,173 | 6/1989 | Porter, III | 128/207.15 |
| 5,029,591 | 7/1991 | Teves | 128/715 |
| 5,040,531 | 8/1991 | Coleman | 128/207.15 |
| 5,067,957 | 11/1991 | Jervis . | |
| 5,069,226 | 12/1991 | Yamauchi et al. | 128/772 |
| 5,090,408 | 2/1992 | Spofford et al. . | |
| 5,096,454 | 3/1992 | Samples . | |
| 5,147,370 | 9/1992 | McNamara et al. | 606/108 |
| 5,176,660 | 1/1993 | Truckai . | |

FOREIGN PATENT DOCUMENTS

| 2426344 | 12/1975 | Germany | 128/207.15 |
|---|---|---|---|
| 933307 | of 1963 | United Kingdom | 128/207.15 |

OTHER PUBLICATIONS

*A new thin-walled non-kinking catheter for peripheral vascular cannulation*, Theodor Kolobow and Warren Zapol, Surgery, vol. 68, No. 4, pp. 625–629, Oct. 1970.
*Silastic ® Endotracheal Tube*, Dow Corning, Don R. Miller, "Tracheal Stenosis Following Prolonged Cuffed Intubation: Cause and Prevention", Annals. of Surgery, vol. 171, No. 2, Feb. 1970.
*Injuries to the neonatal, labyns, front long term endotracheal tube intubation and suggested tube modification for prevention*, Hengerer et al, 1975.
*Laryngeal effects of prolonged intubation*, Bishop, Anesth. Analg., 1984, 63:335–342.

Primary Examiner—Edgar S. Burr
Assistant Examiner—William J. Deane, Jr.
Attorney, Agent, or Firm—Lowe, Price, LeBlanc & Becker

[57] ABSTRACT

An ultra-thin wire reinforced endotracheal tube which includes a novel sealing design adapted to fit in a complementary manner in a subject's larynx. The endotracheal tube includes a laryngeal section which has a cross sectional shape and size that are complementary to a subject's glottis. Preferably, the laryngeal section has an oval or egg-shaped cross section. A plurality of thin, pliable sealing "gills" are provided on the surface of the laryngeal section. The gills provide a fluid tight seal which does not harm a subject's larynx. The endotracheal tube is reinforced with a metallic spring material. In a preferred embodiment, the metallic spring material is a shape memory alloy. The use of a shape memory alloy prevents damage to the endotracheal tube caused by distortion, such as kinking, crushing, etc.

15 Claims, 7 Drawing Sheets

FIG. 1

FIG. 2A — OVAL

FIG. 2B — EGG-SHAPED

THIN WALL ENDOTRACHEAL TUBE

RELATED APPLICATIONS

This application is a Continuation-In-Part of application Ser. No. 07/878,784, filed May 6, 1992, now U.S. Pat. No. 5,305,740, which is a Continuation-In-Part of application Ser. No. 07/758,824, filed Sep. 12, 1991, now abandoned, the complete disclosures of which are expressly incorporated herein by reference.

FIELD OF INVENTION

The present invention is directed to endotracheal tubes, their use and fabrication. More particularly, the present invention is directed to a novel endotracheal tube design that includes a laryngeal section which has a cross sectional shape that is complementary to the cross sectional shape of a subject's larynx. The laryngeal section is provided with seal means which effectively provides a fluid seal between the outer wall of the tube and the trachea.

The present invention is further directed to an ultra-thin walled wire reinforced endotracheal tubing. The ultra-thin walled tubing comprises a polymer tube having incorporated therewith a metallic spring material or a shape memory alloy spring material.

BACKGROUND ART

Endotracheal tubes are widely used in anesthesia and critical care medicine. In use, endotracheal tubes provide access to the upper airways for controlled, assisted ventilation or spontaneous unassisted ventilation with positive end expiratory pressure.

One of the drawbacks of inserting an endotracheal tube into an upper airway of a patient results in the reduction of the lumen of the airway. One cause by which the lumen is reduced is the inability to use the largest possible endotracheal tube for a given patient without subjecting the patient to increased risks. Generally, it is not advisable to insert the largest possible endotracheal tube in a patient since such an attempt will entail many trials and errors which may take additional time which should be avoided especially in critical care or emergency situations.

In addition, the wall thickness of an endotracheal tube needs to be such to provide sufficient strength so as to be safely handled by the using physician or technician during insertion and to maintain the tube stable after insertion. At present, adult endotracheal tubes range between 7 to 9 millimeters in internal diameter with a total wall thickness ranging between 1.4 and 1.5 millimeters. For newborn endotracheal tubes, the decrease in lumen internal diameter as a result of the required wall thickness amounts to approximately 0.5 millimeters or more.

Any decrease in the lumen due to wall thickness of an endotracheal tube has a profound effect on the airway resistance, since the resistance to air flow is inversely proportional to the fourth power of the radius.

As a result of the deficiencies in prior art endotracheal tubes, a need has developed to provide an endotracheal tube having reduced airway resistance so as to facilitate establishment of artificial airways other than those using mechanical ventilators.

Conventional technology used in the fabrication of blood catheters uses either extrusion or dip coating onto mandrels. Extrusion technology has the advantage of low cost, but has little flexibility. With extrusion, the resulting thin wall catheters are rather stiff and are liable to kink or bend and thus obstruct the inner passageway. The dip coating technique used for currently available catheters and tubes is not reproducible in thin wall gauges and, therefore, wall thickness remain substantial.

Currently used endotracheal tubes (ETT) are well standardized worldwide, and are for the most part manufactured from extruded polyvinyl chloride (PVC). Except for the newborn patient population, standard endotracheal tubes have at their distal end an inflatable cuff for an airway seal with the trachea. In addition, there is a limited use for specialty endotracheal tubes to meet the needs of various applications.

For successful use, it is important to provide a good seal between the outer wall of an endotracheal tube and the trachea into which it is inserted. Conventionally, such a seal is provided by using an inflatable cuff attached to the endotracheal tube. Such inflatable cuffs utilize either low or high pressure fluids to cause them to inflate and thus require additional fluid passageways that are connected to the inflatable cuffs.

Unfortunately, the use of inflatable cuffs is sometimes injurious to the trachea, causing pressure necrosis, bleeding, fistula formation, etc. Following removal of endotracheal tubes having inflatable cuffs, particularly following long term use, there is a significant potential for scar formation with resultant tracheal stenosis. Because of the above sequelae, the use of inflatable cuffs is frowned on in conjunction with newborns and small children, because such adverse effects oftentimes are far more debilitating were they to occur in patients other than adults.

As a result of the above problems and concerns and design limitations, endotracheal tubes up to size 5 mm do not presently employ inflatable cuffs. As an adverse side effect to this accepted design which lacks a sealing means, there is likely to be a significant air leak that can at times be very troublesome.

The concept of modifying the shape of a standard endotracheal tube in its laryngeal portion was suggested by Hengerer in 1975 for the purpose of reducing grooving in the vocal cords (Hengerer et al, "Injuries to the Neonatal Larynx from Long-term Endotracheal Tube Intubation and Suggested Tube Modification for Prevention", *Ann. Otol. Rhinol Laryngol.* 1975;84:764–770). Hengerer proposed changing a 2 cm section of endotracheal tube into a triangular shape for use in newborns. Miller et al have suggested attaching silicone rubber rings onto the most distal portion of the endotracheal tube for the purpose of attaining an airway seal within the trachea (but not with the larynx) (Miller et al, "Tracheal Stenosis Following Prolonged Cuffed Inturbation: Cause and Prevention", *Ann. Surg.* 1970;174:283–293). These, and other efforts have been stymied by the enormous difficulties to a very complex problem.

Bishop, on reviewing laryngotracheal injury following prolonged tracheal intubation suggested that the ideal shape of the endotracheal tube at the level of the larynx ought to be pentagonal in cross-section (Bishop, "Laryngeal Effects of Prolonged Intubation", *Anesth. Analg.* 1984;63:335–342); the technology then available made such solution impossible.

While the use of presently available commercial endotracheal tubes is unlikely to have major adverse effects in short term applications, problems encountered in long term orotracheal or nasotracheal intubation have been serious, and have defied solution thus far.

The present invention provides an ultra-thin walled wire reinforced endotracheal tube which provides reduced airway resistance to permit easier breathing by a patient. The ultra-thin walled endotracheal tube comprises a polymer having incorporated therewith a metallic spring material to form a continuous tubing. The combination of the polymer and metallic spring material provides an ultra-thin wall of the tubing which permits the use of an endotracheal tube having similar diameters as prior art tubings but with increased internal diameters and resultant reductions in airway resistance.

The present invention also provides an endotracheal tube design that includes a laryngeal section which has a cross sectional shape that is complementary to the cross sectional shape of a subject's larynx. The laryngeal section is provided with seal means which effectively provide a fluid tight seal between the outer wall of the tube and the trachea.

The present invention further provides a novel sealing means which avoids the use of inflatable cuffs, and which is applicable to endotracheal and similar tubes of all sizes including those having an outside diameter which is less that about 5 mm.

SUMMARY OF THE INVENTION

It is accordingly an object of the present invention to provide endotracheal tubes which establish a fluid tight seal when inserted into a larynx.

Another object of the present invention is to provide endotracheal tubes which have non-circular cross sectional laryngeal portions.

A further object of the present invention is to provide endotracheal tubes which have non-circular cross sectional laryngeal portions with sealing means at the non-circular cross sectional laryngeal portions.

It is a further object of the present invention to provide ultra-thin walled wire reinforced endotracheal tubes.

It is a further object of the present invention to provide endotracheal tubes which are reinforced with shape memory alloy materials.

A still further object of the present invention is to provide an apparatus for and a method of making ultra-thin walled wire reinforced endotracheal tubing having sealing means on an outer wall thereof.

In accordance with these and further objects of the invention which will become apparent as the disclosure thereof is presented below, the present invention provides a two-stage endotracheal tube which includes:

a first generally cylindrical portion having a first diameter;

a second generally cylindrical portion having a second diameter, the second diameter being greater than the first diameter; and a tapered portion connecting the first and second generally cylindrical portions, wherein a length of the second generally cylindrical portion adjacent the tapered portion is non-circularly shaped so as to be complementary to a subject's larynx.

The present invention further provides an ultra-thin walled wire reinforced endotracheal tube which includes:

a generally cylindrical tubular wall of a predetermined length and thickness; and a spring wire material incorporated within the generally cylindrical tubular wall, wherein the spring wire material comprises a shape memory alloy and the thickness of the tubular wall is between about 0.15 mm and 0.35 mm.

BRIEF DESCRIPTION OF DRAWINGS

The present invention will be described with reference to that attached drawings which are given by way of non-limiting examples only, in which.

DESCRIPTION OF THE PREFERRED EMBODIMENTS

The present invention is concerned with endotracheal tubes which provide artificial airways in applications such as anesthesia and critical medicine. According to one embodiment, the present invention provides ultra-thin walled wire reinforced endotracheal tubes which offer advantages over prior art tubing by providing, for the same outer diameter of tubing, an increased inner diameter and reduced airway resistance. By incorporating a metallic spring material with a polymeric material in a thin walled tubing configuration, an endotracheal tube is provided which has sufficient strength to be safely handled by a user. By incorporating a metallic spring made from a shape memory alloy, the resulting endotracheal tube can recover its original shape if crushed, kinked, bent, etc.

By providing a low air resistance endotracheal tube, whereby patient breathing is made easier, patients may be able to utilize a simpler means of respiratory assistance such as continuous positive airway pressure (CPAP) rather than mechanical ventilation means.

In the newborn patient population, the lowering of airway resistance is of vital importance since newborns are more likely to become exhausted or have further difficulty in breathing by using prior art endotracheal tubes having significant airway resistance. By utilizing the inventive ultra-thin wall wire reinforced endotracheal tubes in newborn patient application, significant reductions in airway resistance are attainable.

In addition, developments and other alternatives for mechanical ventilation such as intratracheal pulmonary ventilation which include a reduction in dead space ventilation and a decrease in airway pressure favor the utilization of establishment of artificial airways having reduced resistance to air flow. As will be described hereinafter, the inventive tubing reduces the wall thickness by 50–80%, thereby resulting in a two- to four-fold decrease in air flow resistance.

In addressing the issue of airway sealing, the present invention provides a novel endotracheal tube design that includes a laryngeal section which has a cross sectional shape that is complementary to the cross sectional shape of a subject's larynx. This laryngeal section of the endotracheal tube has a non-circular cross sectional shape which deviates from the traditional design and allows for a tighter, natural seal at the larynx when inserted therein.

The present invention is also directed to a sealing means for endotracheal tubes which are applied to the outer surface of the non-circular laryngeal section to ensure a fluid tight seal once the laryngeal section is received in a subject's larynx.

As discussed in detail below, the sealing means of the present invention includes a plurality of thin, soft, pliable gills or flanges which are provided on the outer wall of the endotracheal tube. The gills or flanges are sufficiently flexible to form a fluid tight seal between the outer wall of the tubular member and the corresponding or adjacent inner wall of a lumen into which the tubular member is inserted and positioned. The gills or flanges are made of a suitably pliable material such as polyvinyl chloride, silicone rubber, polyethylene, and the like, which are biocompatable for their intended use.

Conventional endotracheal tubes traditionally are made from sections of extruded PVC tubing, or else are produced by a dipping method. It is well known that conventional endotracheal tubes impart a significant increase in upper airway resistance, particularly so if for technical or other considerations one chooses a smaller endotracheal tube than otherwise might have been indicated. The present invention allows for the production of endotracheal tubes with a greatly reduced airway resistance. By keeping the wall thickness around 0.2 mm, the present invention greatly increases the internal diameter of the endotracheal tubes. In addition, the present invention provides an ultra-thin two-stage endotracheal tube (UTTS ETT) by which further reduction of the airway resistance is achieved. For example, instead of a 7.5 mm standard endotracheal tube, a ultra-thin two-stage endotracheal tube with the same outside dimensions at its distal end converts into what amounts to a 10.8 mm conventional endotracheal tube based on pressure/flow characteristics; the air flow resistance for the latter ultra-thin two-stage endotracheal tube is virtually identical to the air flow resistance of the major upper airways in a non-intubated, healthy adult male.

The new endotracheal tubes of the present invention are one third the weight of a standard endotracheal tube, incomparably more flexible, non-kinking, crush resistant (with shape memory alloy reinforcement), and do not impart a significant torque on the distal end when the proximal end is manually twisted.

The present invention diverges from traditional means of attaining a seal with the upper airways. In this regard, the shape of the laryngeal portion of the endotracheal tube is formed into an oval (or egg shape), to more accurately approximate the true anatomy of the internal laryngeal structures. This was found to lead to a decrease in point pressure on the vocal processes and other structures of the larynx, and reduce pressure necrosis. In addition, because of the much greater flexibility imparted to the endotracheal tube when the wire reinforcement is incorporated, there is a reduction of transmitted torque, and an elimination of motion of the endotracheal tube within the larynx. By providing a better, more stable, fit of the endotracheal tube, it is possible to fill voids around the endotracheal tube within the larynx with sealing means which comprise doughnut (toroidal) shaped rings of thin, soft plastic film, which readily deformed to fill small voids. Invariably, the presence of entrained tracheal mucous greatly enhanced this sealing function, resulting in what amounts to a self-fitting, no pressure seal at the level of the larynx. By avoiding the use of an inflatable cuff, it is possible to decrease tracheal injury following tracheal intubation.

When conventional endotracheal tubes (with cuff removed or deflated) were compared with the present endotracheal tubes of same outside diameter and with the attached gills, there was consistently no air leak with the latter, at least to pressures of 30 cm $H_2O$, while there was a prohibitive leak in the former. This suggests that it was possible to eliminate the conventional inflatable cuff, which is the cause of tracheal lesions, and to move the site of the airway seal to the more rigid structures of the larynx in the form of an accommodating, "no pressure" seal system. The present invention decreases the contact pressure on the laryngeal structures. This reduces/eliminates necrosis by distributing the load over a much larger area of contact. In addition, the contact is cushioned by interposing the "gills" (made slippery by ever present mucus).

According to one preferred embodiment, the endotracheal tubes of the present invention were reinforced with a new material, Nitinol wire. Unique among alloys, Nitinol superelastic memory alloy exhibits remarkable kink-resistance, it renders the wire reinforced endotracheal tube truly crush proof, a feature of great importance when dealing with endotracheal tubes of a wall thickness of about 0.2 mm or less.

Figure 1:
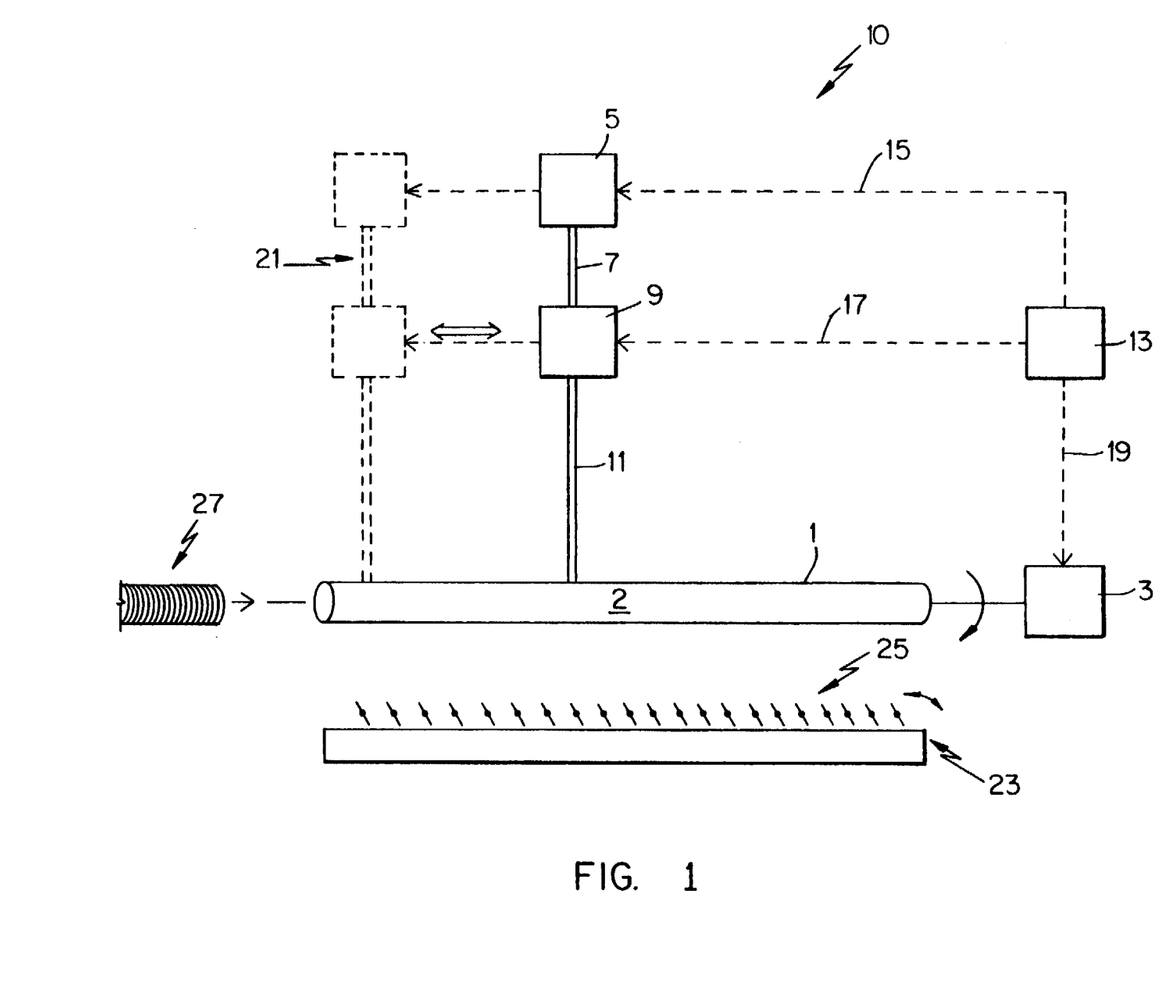
FIG. 1 shows a schematic representation of one embodiment of the apparatus utilized for making the ultra-thin walled wire reinforced endotracheal tubing.

With reference now to FIG. 1, a schematic representation of an apparatus adapted for making ultra-thin walled wire reinforced endotracheal tube is illustrated. The apparatus is generally designated by the reference numeral 10 and is seen to include a cylindrical mandrel 1 having a release agent coating on the surface 2 thereof. The release agent 2 is designed to facilitate removal of the ultra-thin walled wire reinforced endotracheal tubing from the cylindrical mandrel 1. The release agent may be any agent known in the art such as Teflon ®. The cylindrical mandrel may be made of any material having sufficient strength to provide support for the tubing, preferably a steel rod.

The cylindrical mandrel is connected to a lathe means 3 which includes drive means therewith to rotate the mandrel at a predetermined speed. Of course, any known means capable of rotating a cylindrical mandrel may be utilized in substitution for the lathe 3.

The apparatus for making the ultra-thin walled wire reinforced endotracheal tubing also includes a polymer source means 5 which supplies a dissolvable polymer such as polyurethane Lycra ® under pressure to a metering pump 9 via the line 7. The polymer source means 5 may be a closed container including a source of inert gas to provide the pressure to supply the dissolved polymer to the metering pumping 9. Preferably, the source of the pressure is a dry nitrogen or other inert gas.

The metering pump 9 includes a nozzle 11 made out of a flexible tubing such as Teflon ®. The tubing 11 should have sufficient flexibility and thickness to follow the contours of the cylindrical mandrel 1 and float on the polymer layer as it emerges from the nozzle. The flexibility of the tubing 1 may be enhanced by the addition of a spring material surrounding the tubing. The metering pump 9 may be a gear fluid pump designed to meter a solution of polymer onto the mandrel.

The polymer source means 5 and metering pump means 9 also include a cross feed means which permits the source means 5, metering means 9 and nozzle 11 to traverse the length of the mandrel 1. As illustrated by the reference numeral 21 in FIG. 1, the source means 5, metering pump 9 and nozzle 11 are displaced along the longitudinal axis of the cylindrical mandrel 1. The longitudinal movement of the nozzle 11 permits that polymer to be continuous applied to the mandrel 1 over a preselected pattern. When fabricating a two-stage endotracheal tube according to the present invention, the mandrel 1 will be provided with an appropriate contour. In such a case, suitable mechanical positioning means can be used to move tubing 11 along the contour of the mandrel 1.

A control means 13 is provided that regulates the deposition of the polymer on the mandrel 1. The control means 13 is connected to the polymer source means 5 via the line 15, the metering pump 9 via the line 17 and the lathe 3 via the line 19. By controlling the rotation of the mandrel 1 via the lathe 3 and the amount of polymer deposited on the mandrel 1, the thickness of polymer applied to the mandrel or wall thickness of the ultra-thin walled and wire reinforced endotracheal tubing may be controlled and varied. The control means 13 also provides control over longitudinal traversing of the nozzle 11 and associated components and the cylindrical mandrel 1. It should be understood that, although the nozzle 11, metering pump 9 and polymer source means 5 are depicted as longitudinally traversing the length of the cylindrical mandrel 1, in another embodiment, the polymer source means 5 may be stationery with the metering pump 9 and nozzle 11 traversing the length of the mandrel 1. It should be understood that the mechanism for providing the longitudinal traversing movement of either the metering pump 9 and nozzle 11 or these components with the polymer source means 5 are well recognized in the prior art. For example, these components may be longitudinally traversed using a drive means and rack and pinion gearing. Likewise, a similar known mechanism can be incorporated to move nozzle 11 to follow the contour of the mandrel 1 if necessary.

The apparatus 10 also includes a heating means 23 which supplies heat such as hot air to the mandrel 1 to dry the polymer solution after deposition on the mandrel.

The heating means may a strip heater or other known heating means. The heating means 23 may also include individually adjustable baffles 25 which facilitate directing the hot air toward the mandrel 1. The adjustable feature of the baffles 25 permit varying the amount of drying air along the length of the mandrel 1. For example, when producing a tapered endotracheal tube, certain areas of the tube having increased wall thickness require a higher heat input for drying purposes. In this situation, the individually adjustable baffles are arranged to direct more hot air to the portion of the cylindrical mandrel having the endotracheal tube with increased wall thickness.

FIG. 1 also depicts a coil spring 27 which is designed to be inserted over the Teflon ® coated cylindrical mandrel 1. The spring 27 may be manually inserted over the rod or, alternatively, by known mechanical means. As an alternative embodiment, the spring material may be in the form of an unwound wire or flat material and be wound around the cylindrical mandrel in a known fashion. As will be described hereinafter, the spring 27 may be applied to the mandrel 1 after or during the deposition of the polymeric material.

Figure 9:
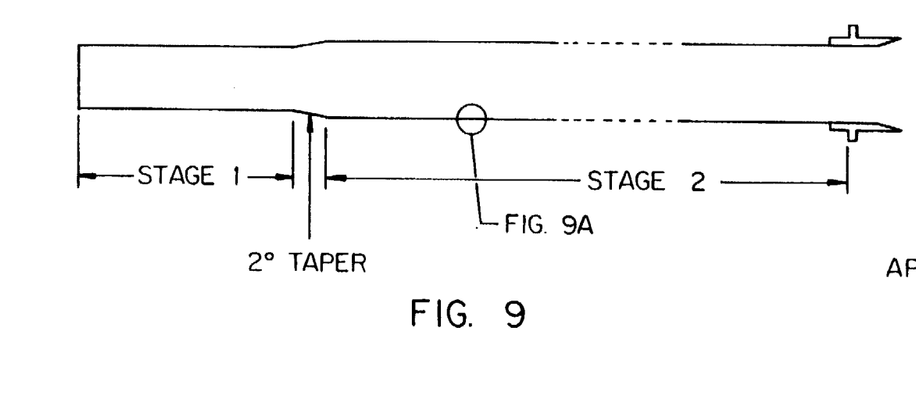
FIG. 9 is a schematic cross sectional side view of an ultra-thin two-stage endotracheal tube according to the present invention.
Figure 9A:
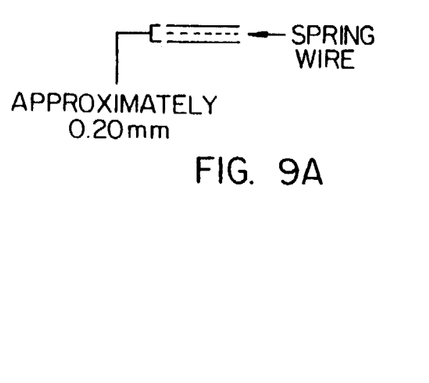

The method of making the ultra-thin walled wire reinforced endotracheal tubes according to the present invention will now be described. First, a mandrel is machined from a suitable material such as steel to the exact internal dimensions of the desired endotracheal tube. According to one embodiment, the mandrel can be of the same dimension throughout as in conventional endotracheal tubes (ultra-thin ETT, UT ETT). In another embodiment the mandrel can be provided with a short section with a smaller diameter (to rest within the trachea), and gradually tapering at a 2° angle to a larger diameter for the oropharyngeal section (ultra-thin two-staged ETT, UTTS ETT) (FIG. 9). Following this, the mandrel is placed in a rotating lathe and a solution of polyurethane (Lycra ®) in a compatible solvent, e.g. dimethylacetamide (DMA) is metered onto the rotating mandrel. A typical concentration of polymeric material would range between 10–30 weight percent polymer in the solvent, with about 15 weight percent polymer being ideal.

This range is only exemplary and greater or lesser concentrations of polymeric material may be utilized depending on the particular polymer being employed. The dissolved polymer is supplied to a metering pump under pressure such as dry nitrogen. The metering pump, such as a fluid gear pump, meters the dissolved polymer unto the rotating surface of the mandrel while the nozzle traverses the length of the cylindrical mandrel. The deposited polymer is permitted to air dry, or alternatively, dry by application of a source of heat such as a strip heater or the like. This sequence may be repeated if an increased thickness of polymeric material is desired on the surface of the cylindrical mandrel.

By choosing a particular rate of deposition of polymeric material, the solvent evaporation rate can be optimized such that one layer of polymer can be deposited onto the previously deposited and dried layer to build up thickness. In a further embodiment, successive deposition of several layers of polymeric solution may be performed while traversing the cylindrical mandrel on a single run. In this embodiment, a plurality of nozzles may be utilized which are spaced apart from each other such that following nozzles are depositing polymeric material to an already dried polymeric material layer.

Once the initial layer or layers of polymeric solution are deposited on the cylindrical mandrel a spring material, preferably a stainless steel spring or a shape memory alloy spring, is applied to the cylindrical mandrel. In one embodiment, the spring may be in an uncoiled configuration, either flat or round in size, and wound around the polymer-coated mandrel by known mechanical means. Alternatively, the spring may be provided in a pre-coiled configuration and inserted over the mandrel. In further embodiments, the spring material may be wound around the mandrel or inserted thereover simultaneously with the application of the polymer solution.

The choice of the number of windings per inch for the spring or the diameter or cross-sectional area of the spring material may vary depending upon the desired spring properties and flexibility of the ultra-thin walled wire reinforced endotracheal tube. Furthermore, it should be understood that the spring material cross-sectional area, or diameter if the spring material is round, should be sized to provide the ultra-thin walled wire reinforced endotracheal tubing having a reduced wall thickness while maintaining sufficient strength to avoid kinking or bending during handling and subsequent constriction of an airway passage. According to one exemplary embodiment a flat 0.1×0.5 mm wide ribbon of work hardened stainless steel #304 spring wire at a pitch of 24/inch was wound on the polymer coated the mandrel.

In further embodiments of the invention, a shape memory alloy such as Nitinol is incorporated as the reinforcing wire. As discussed above, the properties of shape memory alloys allow fabrication of endotracheal tubes that are crush proof, i.e. following manual occlusion, recovery was complete.

Once the spring wire is applied to the mandrel, further deposition of polymeric material may be performed to yield a smooth outside surface having the desired final diameter. After application, the polymeric material is first air dried, and then the mandrel is contacted with circulating hot air for final cure. According to one preferred embodiment, the total wall thickness, including wire reinforcement, is approximately 0.2 mm.

Figure 2A:
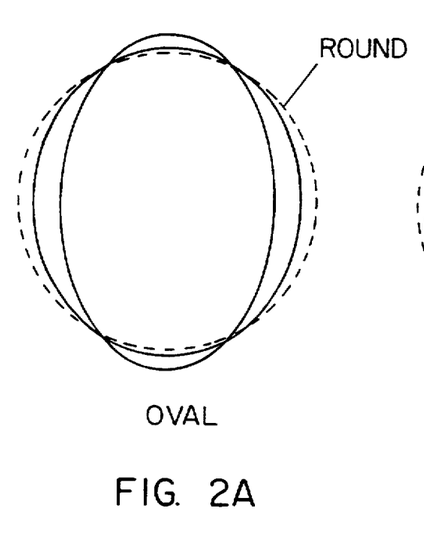
FIG. 2 is schematic cross sectional view of a laryngeal section of an endotracheal tube which depicts various changes in shape applicable to the present invention.
Figure 2B:
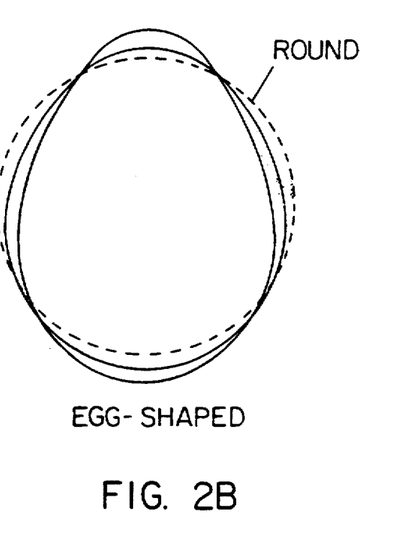
Figure 3:
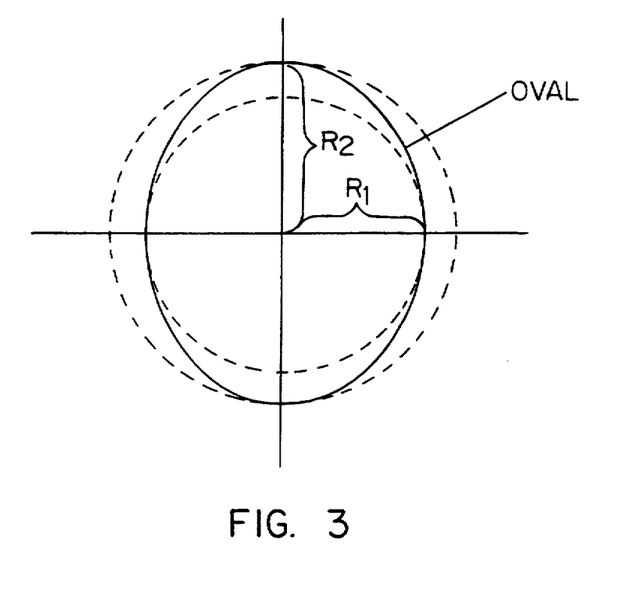
FIG. 3 is schematic cross sectional view of a laryngeal section of an endotracheal tube which depicts an oval shape.

Following final cure, the body of the endotracheal tube is removed from the mandrel. Endotracheal tubes reinforced with non-shape memory alloy materials, e.g. stainless steel wire were then placed in a press which shaped a 4–5 cm section of the second stage of the ultra-thin two-stage endotracheal tube (which was to rest within the larynx) in such manner that it became oval (or egg shaped) in cross-sectional view as illustrated in FIG. 2. During this shaping process, the lesser axis $R_1$ is reduced in width to the approximate outside diameter of the first stage of the ultra-thin two-stage endotracheal tube, while the greater axis $R_2$ is proportionately increased as depicted in FIG. 3. It was the purpose of this design to shape the endotracheal tube to better conform to the approximate anatomical dimensions of the airway at the level of the vocal processes and the larynx, rather than to adhere to the traditional round endotracheal tube design, i.e. to shape the endotracheal tube so that it would better match the longer antero-posterior dimension of the glottic opening, and be narrower in the transverse width. Following trimming and finishing operations, the endotracheal tubes containing the shape memory alloy springs were heat set to a desired curved configuration. It is pointed out that while oval or egg-shaped laryngeal sections were provided according to a preferred embodiment, other non-circular shapes including triangular, pentagonal, and other polygonal shapes can be used since these shapes are more similar to the cross section of a larynx than a circular shape.

When a shape memory alloy spring is used, it is necessary to form the shape memory alloy into a desired configuration and then heat or apply electrical stimulation to the shape memory alloy in order to "set" the shape memory alloy in the desired shape. Thereafter, once deformed, the shape memory alloy will return to the desired configuration. Such means of forming shape memory alloys is known and can be applied before the shape memory alloy material is applied on the mandrel. Any suitable shape memory alloy can be used according to the present invention, including, for example Ti-Ni alloys (including Nitinol) and Cu-Zn-Al alloys.

After the polymer has been applied and cured, the sealing means described below are positioned on the formed polymer tubing either before or after the tubing is removed from the mandrel. The sealing means are fixed to the tubing by means of a suitable, biocompatable cement, selected from those known in the art. According to another embodiment, the sealing means may be positioned on the tubular member prior to complete curing of the polymer. Thereafter, the curing of the polymer may be used to secure the sealing means. Other suitable means such as welding or heat sealing the sealing means on the tubular member could also be used.

The seal means for the endotracheal tube can be vacuum molded from 0.025 or 0.075 mm thick soft, pliable polyurethane sheets to provide a series of doughnut shaped discs (referred herein as "gills" or "flanges"), which are solvent cemented onto the endotracheal tube. When the endotracheal tube is provided with a non-circular laryngeal section, the seal elements are attached to this portion of the endotracheal tube. (There are no "gills" placed on the tracheal portion of the endotracheal tube.) The external diameter of those "gills" should be about 50–100% larger than the outside diameter of the endotracheal tube. The purpose of the "gills" is to provide in effect a "no pressure" seal at the level of the larynx, to help reduce/eliminate possible air leaks from around the endotracheal tube.

Figure 4A:
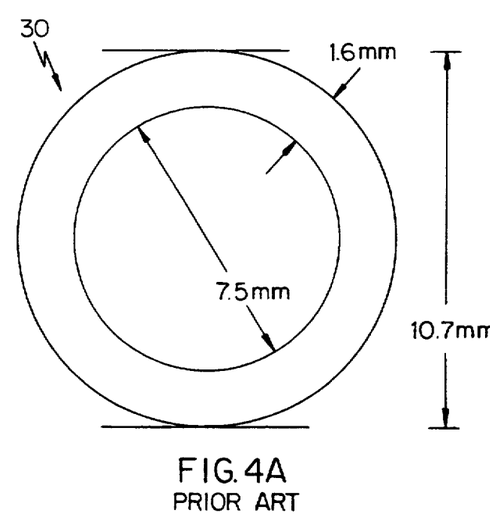
FIG. 4A shows an end view of a prior art endotracheal tube.
Figure 4B:
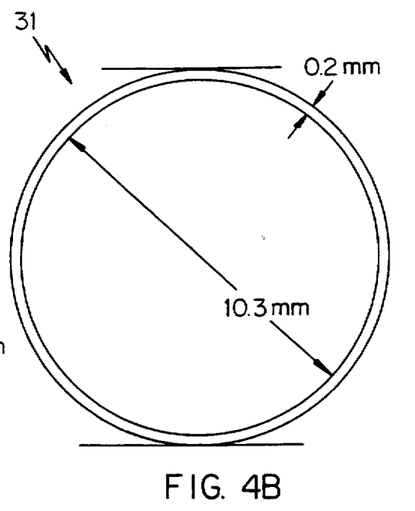
FIG. 4B shows an end view of an endotracheal tube according to the present invention.

With reference to FIGS. 4A and 4B, a comparison is illustrated between prior art endotracheal tubes and the ultra-thin walled wire reinforced endotracheal tubing of the present invention. As can be seen from FIG. 4A, the prior art endotracheal tube having an outer diameter of 10.7 millimeters has an inner diameter of 7.5 millimeters due to the wall thickness of 1.6 millimeters. In contrast, the ultra-thin wall wire reinforced endotracheal tubing of the present invention may be made having the same outer diameter of 10.7 millimeters but with an increased inner diameter of 10.2 millimeters as a result of the reduced wall thickness of 0.2 millimeters.

Figure 5A:
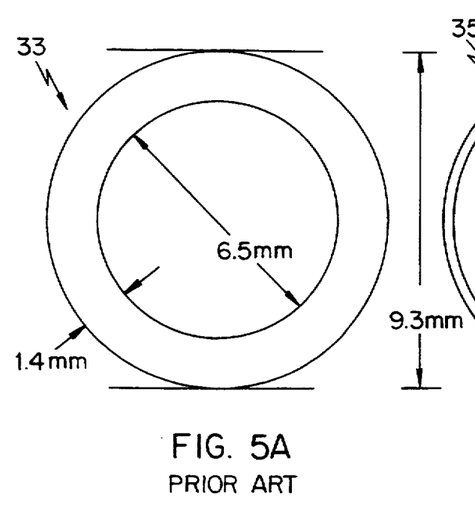
FIG. 5A shows an end view of another prior art endotracheal tube.
Figure 5B:
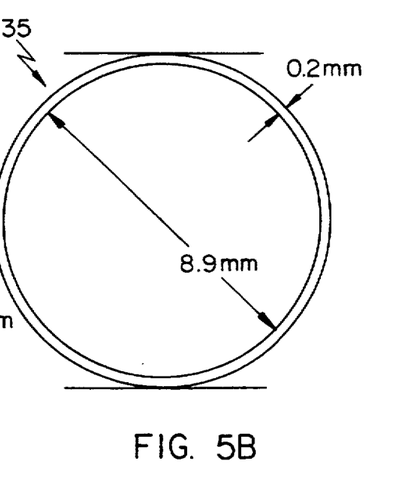
FIG. 5B shows an end view of a smaller size ultra-thin walled wire reinforced endotracheal tube of the present invention.

Referring to FIGS. 5A and 5B, a similar comparison is made wherein the prior art endotracheal tubing 33 is compared to the ultra-thin walled wire reinforced endotracheal tubing 35 of the present invention. In this manner, the prior art endotracheal tubing 33 having an outer diameter of 9.3 millimeters has an inner diameter of 6.5 millimeters. The ultra-thin walled wire reinforced endotracheal tubing 35 has an increase in the inner diameter to 8.8 millimeters for the same 9.3 millimeter outside diameter.

Figure 6:
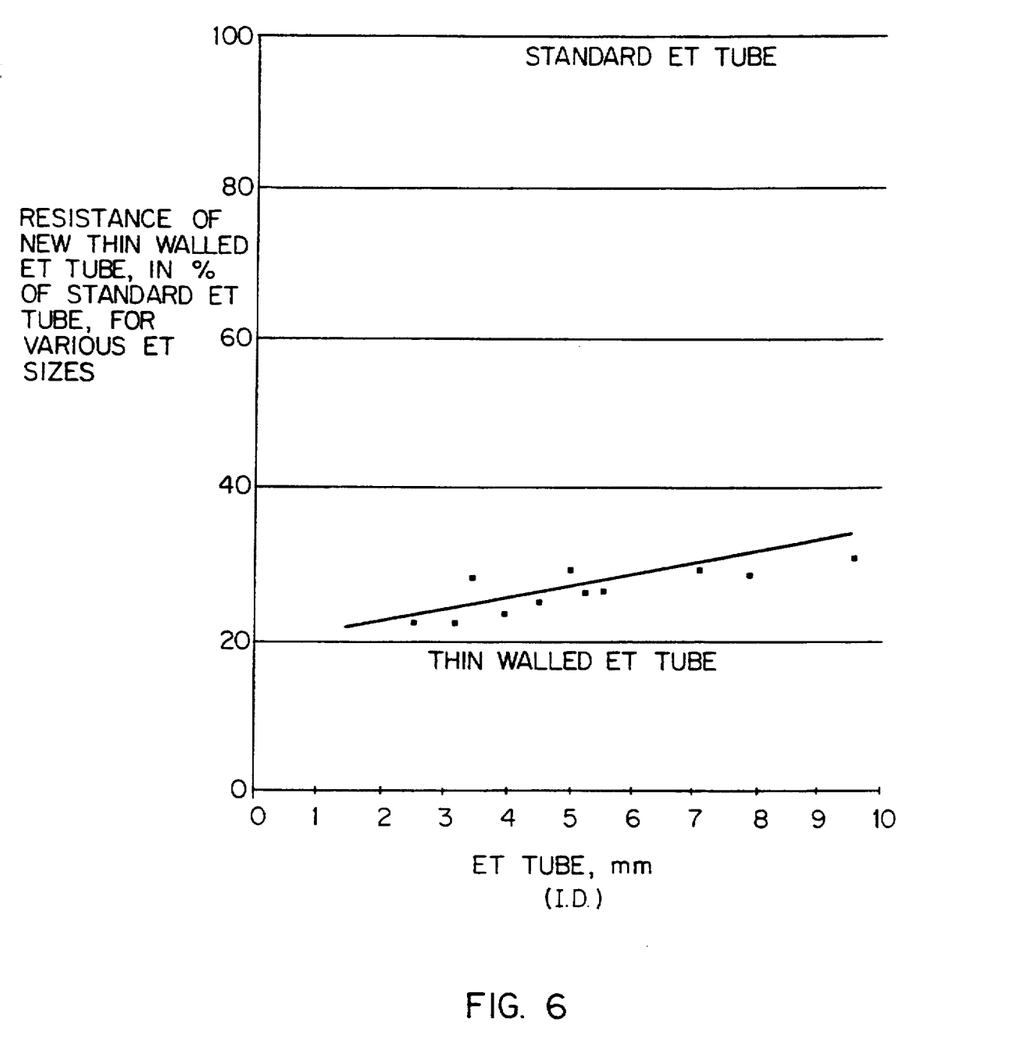
FIG. 6 shows a graph comparing air resistance in the inventive ultra-thin walled endotracheal tube as compared to prior art endotracheal tubes.

With reference now to FIG. 6, a graph is depicted which compares standard endotracheal tubes such as those depicted in FIGS. 4A and 5A with the ultra-thin walled wire reinforced tubing of the present invention having a wall thickness of approximately 0.2 millimeters. The graph compares the resistance of the inventive thin walled endotracheal tubing as a percent of the air resistance of the standard endotracheal tubing for a range of endotracheal tubing based upon inner diameters. As can be seen from the graph in FIG. 6, the inventive thin walled endotracheal tubing results in a substantial decrease in resistance as compared to prior art endotracheal tubing. In addition, air flow resistance is further lowered for smaller sized endotracheal tubes which provides reduced air resistance in endotracheal tubing adapted for newborn patients.

Figure 7:
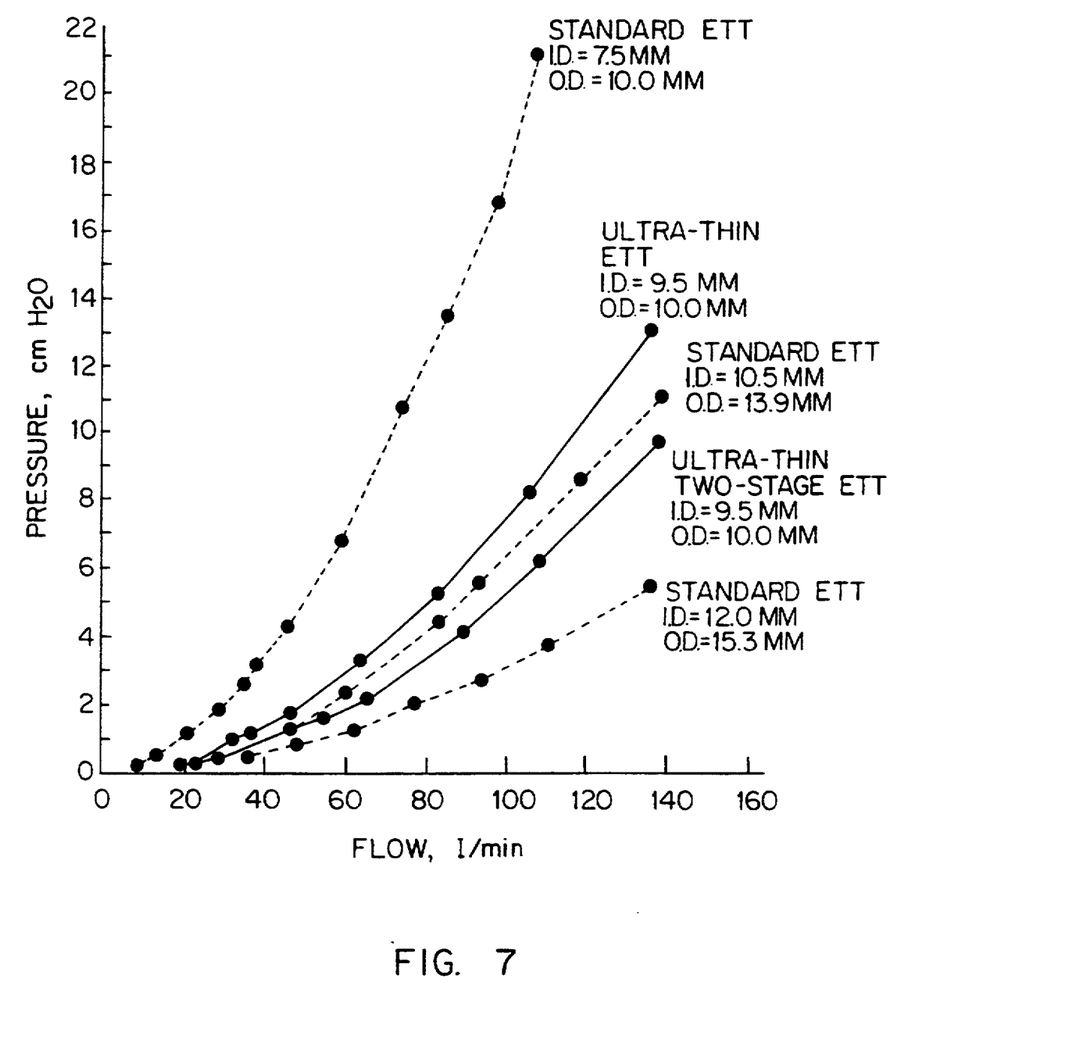
FIG. 7 shows a graph comparing pressure/flow studies of various endotracheal tube designs.

In vitro pressure/flow studies were performed using various sizes of the endotracheal tubes of the present invention. Pressure/flow studies were also performed on standard, commercially available endotracheal tubes from various manufacturers (Sheridan, Mallinkrodt) The results of these in vitro studies are depicted in FIG. 7. From pressure/flow curves it became possible to compute static air flow resistance for all endotracheal tubes, at given air flow. As the pressure flow curves of commercially available endotracheal tubes did not differ much from manufacturer to manufacturer, they were listed as "standard endotracheal tubes". Because of great difference in wall thickness between standard endotracheal tubes and the endotracheal tubes of the present invention, it was pointless to equate the present endotracheal tubes by the internal diameters. Rather, we chose to equate the present endotracheal tubes with the same, or a hypothetical standard endotracheal tube (the "equivalent standard endotracheal tube") that had the same pressure-flow characteristics. See Table 1 below.

Figure 8:
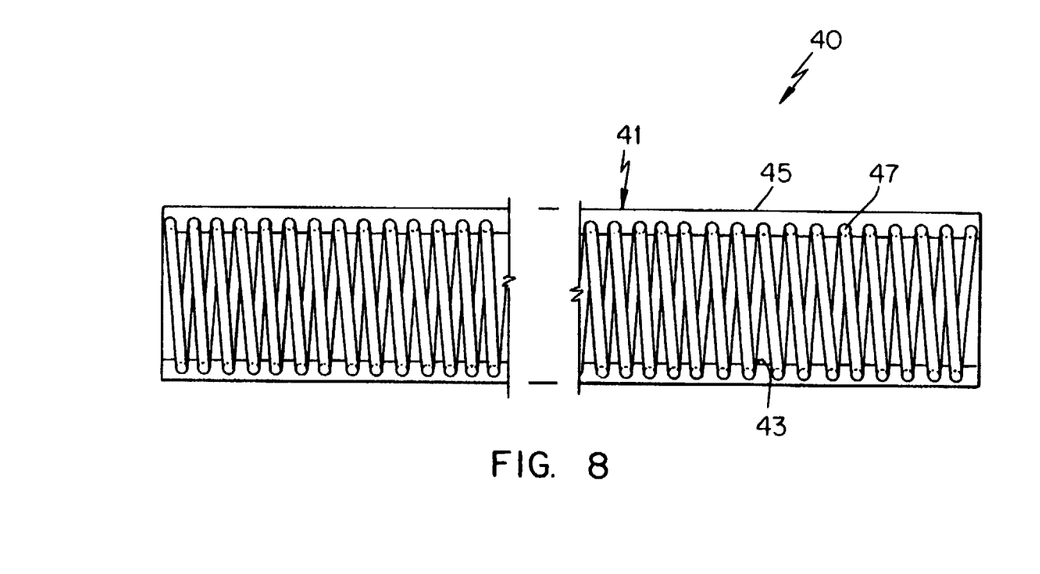
FIG. 8 shows an exemplary ultra-thin walled wire reinforced endotracheal tube showing the spring material incorporated in the endotracheal tubing wall.

With reference now to FIG. 8, an exemplary ultra-thin walled wire reinforced endotracheal tubing is generally designated by the reference numeral 40. The thin walled wire reinforced endotracheal tubing includes a tubing wall 41 having an inner surface 43 and outer surface 45. Incorporated within the tubing wall 41 is a spring 47. The diameter of the spring material 47 is sized in conjunction with the applied layers of polymeric material to provide the minimum wall thickness while maintaining sufficient strength to permit handling of the endotracheal tube. As disclosed above, a wall thickness of about 0.2 millimeters is attainable using the inventive method and apparatus for making the ultra-thin walled wire reinforced endotracheal tubing. The wall thickness of about 0.2 mm is a preferred thickness with the wall thickness ranging between about 0.1 mm and 0.5 mm. A preferred range for the wall thickness includes between about 0.15 mm and 0.35 mm. For a given wall thickness of 0.2 millimeters, it should be understood that the diameter of the wire spring material is less than the wall thickness to provide a polymeric layer along the inner and outer surfaces, 43 and 45 respectively of the tube 40. Alternatively, the wire spring material when positioned on the cylindrical mandrel prior to deposition of polymeric material may form part of the inner surface 43 of the tubing 40.

FIG. 9 is a schematic cross sectional side view of an ultra-thin two-stage endotracheal tube according to the present invention. As depicted in FIG. 9, the ultra-thin two-stage endotracheal tube includes a first stage portion (stage 1) which has a diameter compatible to a subject's trachea and a second stage portion (stage 2) which has a diameter compatible to a subject's oropharyngeal structure. The first and second stage portions are connected together by a tapered portion which is tapered at about 2°.

The apparatus and method of making the ultra-thin walled wire reinforced endotracheal tubing provides a endotracheal tube having a thin wall thickness not attainable in prior art endotracheal tube making apparatus or methods. The inventive apparatus and method also provide flexibility in adapting the manufacture of the inventive endotracheal tubing for various configurations for operating conditions such as an eccentric or slightly out of round mandrel. By having the nozzle of the metering pump 9 float or follow the contour of the mandrel, any slight out of roundness and/or eccentricity of the mandrel can be easily accommodated without effecting the quality of the tube.

In addition, the method of applying the polymer solution along the length of the mandrel permits programming of the control means to achieve different tubing configuration. For example, by increasing the flow rate of the dissolved polymer or reducing the rotation of the mandrel in conjunction with controlling the travel of the nozzle 11 along the mandrel, varying thicknesses of wall tubing may be obtained. By programming of more layers of different thicknesses on different parts of the mandrel, utilizing the control means, tapered endotracheal tubes may be manufactured. Alternatively, the mandrel 1 may be made having a tapered configuration wherein a tapered spring material may be used in conjunction with a uniform coating to produce a tapered tube having a uniform wall thickness.

Figure 10A:
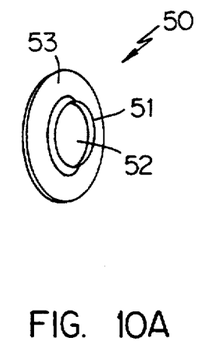
FIG. 10A is a perspective view of a sealing means according to one embodiment of the present invention.
Figure 11:
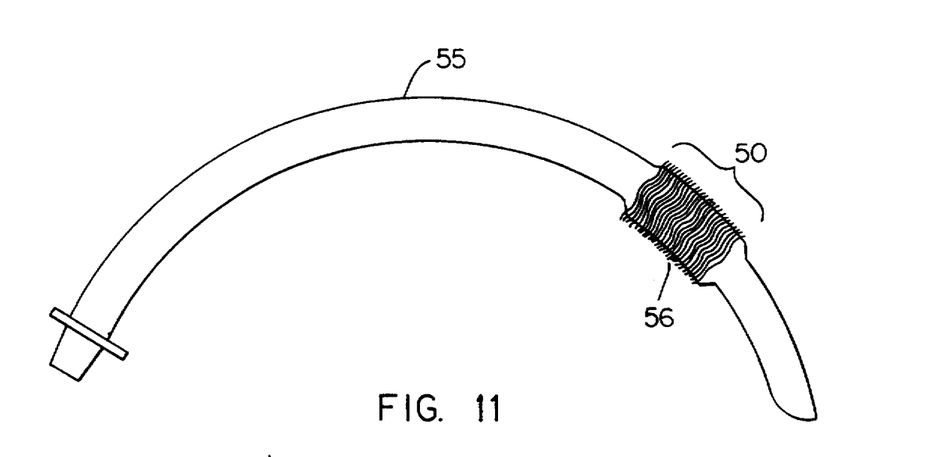
FIG. 11 shows an endotracheal tube according to one embodiment of the present invention which includes the sealing means of FIG. 10A.
Figure 11A:
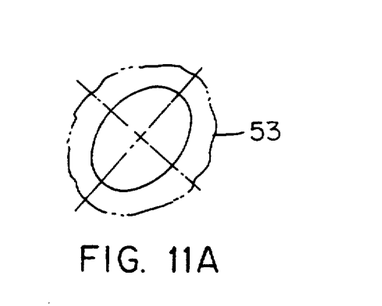

FIG. 10A shows a sealing means 50 according to one embodiment of the present invention. As shown, the sealing means 50 is a gilled- or flanged-collar. The collar portion 51 includes a through-bore 52 which allows a tubular member to be inserted within the sealing means 50 and fixed thereto as shown in FIG. 11. The gill or flange 53 of the sealing means 50 is a thin, soft, pliable element made of a suitable biocompatable plastic material such as polyvinyl chloride, silicon rubber, polyethylene or the like, and is preferably integral with the collar portion 51, which may be made of a similar plastic material.

In a preferred embodiment, the gill or flange 53 of the sealing means 50 is made of a thin, e.g., 0.05 mm polyurethane, vacuum formed, and then cut and punched to an appropriate size. Other suitable methods of fabricating the sealing members, such as injection molding, separately fabricating and attaching the collar and flange portions, etc. could also be utilized. The thickness of the gill or flange portion should be relatively thin to ensure that the gill or flange is suitable soft and pliable. According to one embodiment of the present invention, the gills or flanges were as thin as about 0.01 mm. In another embodiment the gills or flanges were between about 0.025–0.05 mm thick. While the thickness of the gills or flanges can be greater than 0.05 mm, depending on the pliability of the material from which they are formed, the limiting factor on this thickness is the ability of the gills or flange portions to provide the desired seal discussed above.

Figure 10B:
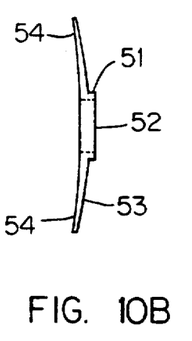
FIG. 10B is a cross sectional view of the sealing means of FIG. 10A.

FIG. 10B show a cross section of the seal means of FIG. 10A. As shown, the gill or flange 53 extends from collar portion 51. The cross sectional area of the gill or flange 53 is tapered as illustrated so as to be thicker near the collar 51. The free edge 54 of the gill or flange 53 is feathered as shown. The gill or flange 53 may extend perpendicular from the collar 51 either straight or with a slight curve. The curved shape of the gill or flange 53 which is illustrated in FIG. 10B may provide a better seal when a tubular member having curved gills or flanges 53 is first inserted then backed out a short distance to reverse the curve of the gills or flanges 53 from the direction in which they are oriented when being inserted. In this embodiment, the curve shape can provide a small bias force to the seal means.

For an endotracheal tube, the diameter of the gills or flange portions can range from as small as 0.5 mm to 1 cm or more. The diameter or the gills or flanges can be determined from the outside diameter of the tubular member and the inner diameter of the lumen and should generally be about 50–100% larger than the outside diameter of the endotracheal tube.

According to one design, the diameter of the gills or flanges as measured from the collar to the free end is between about 0.5–5.0 mm. The thickness of the gills or flanges at the collar is about 0.06 mm and the feathered edge is about 0.02 mm thick. Equally well, they could be of even thickness throughout.

FIG. 11 shows an endotracheal tube 55 having the sealing means 50 of FIG. 10A attached thereto. As shown, the sealing means 50 are located at a laryngeal section 56 of the endotracheal tube 55 which has a non-circular cross section. In FIG. 11, twenty-two sealing members are shown on the endotracheal tube 55. However, it is noted that any number of sealing means including one, ten, twenty, thirty or more could be utilized.

Figure 12:
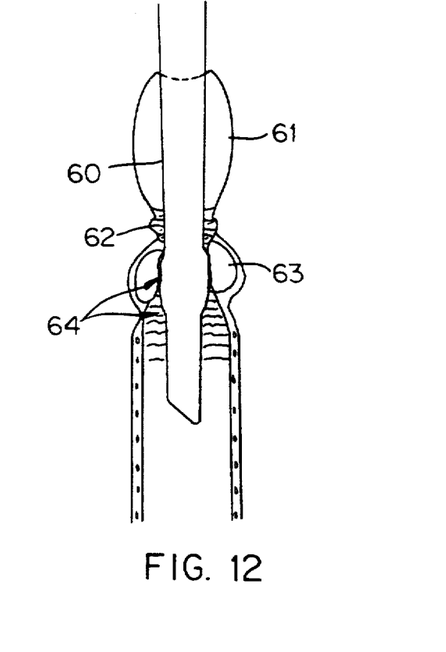
FIG. 12 shows an endotracheal tube with a sealing means according to the present invention positioned in a larynx-trachea.

FIG. 12 shows an endotracheal tube according to the present invention which is positioned in a larynx-trachea. As shown in FIG. 12 the endotracheal tube 60 is inserted through the epiglottis 61, vocal cord area 62 and the cricoid 63. The gills or flanges 64 of the sealing means (collars are not shown) which are located within the narrow or constricted portion of the lumen adjust to the inner diameter of this portion of the lumen due to their pliability and form a seal between the endotracheal tube 60 and the inner wall of the lumen.

It has been found that the gills or flanges will accommodate the anatomy of the trachea and that some tracheal bronchial secretions are likely to be entrapped between the gills or flanges, thus assisting sealing off air-/oxygen leakage. More importantly, there is almost negligible pressure on the adjacent epithelium of the trachea. This greatly reduces or eliminates tracheal wall injury. It is further noted that the tapering of the gills or flanges as discussed above helps protect the tracheal epithelium from possible undue physical trauma.

As can be understood from FIG. 12, the diameter of the gills or flanges 64 of the sealing means should be substantially larger than the distance between the outer wall of the tubular member 60 and the inner wall of the lumen.

The sealing means of the present invention have a particular advantage in that they can be utilized in conjunction with endotracheal tubes which are less than about 5 mm in diameter. Heretofore, no sealing means, e.g. inflatable cuffs, was provided for such small endotracheal tubes. Of course, in addition to being particularly useful for small (less than about 5 mm) diameter endotracheal tubes, the sealing means of the present invention could also be suitable sized and utilized with larger diameter tubes.

The sealing means of the present invention has been found to be especially useful in conjunction with the above-discussed ultra-thin wall walled wire reinforced endotracheal tubes. This combination provides endotracheal tubes which have low airway resistance and a maximum inside diameter for a given outside diameter. By utilizing the sealing means of the present invention in stead of inflatable cuffs on these ultra-thin walled endotracheal tubes, possible deformation of the tubes caused by inflating or over inflating of the cuffs can be avoided. Moreover, as in the case of any type of endotracheal tube, use of the sealing means of the present invention in place of inflatable cuffs avoids the need for additional fluid passages needed to inflate and deflate the cuffs, thus allowing reduction of the overall diameter of the tubes.

The following example is presented to illustrate features and characteristics of the present invention which is not to be considered as limited thereto.

EXAMPLE

After premedication with pentobarbital, the trachea of 26–28 kg sheep were incubated with a commonly available hollow introducer, over which an ultra-thin two-stage endotracheal tube of the present invention was readily glided into place. The location and position of the oval (egg shaped) portion of the endotracheal tube was carefully verified by direct vision, and by roentgenographic films. The endotracheal tube was then secured to a bite block. The sheep were maintained under general anesthesia using phenobarbital at 4 mg/kg h, and pancuronium bromide at 0.06 mg/kg h. The sheep were placed on a Siemens 900 C Servo Ventilator, and were ventilated at a respiratory rate of 15/min, and an initial tidal volume (VT) of 8–10 ml/kg in the volume controlled mode. To achieve a higher peak inspiratory pressure (PIP), VT was increased so as to raise PIP in increments of 5 cm change $H_2O$, up to 50 cm $H_2O$. PEEP was thereafter raised to 5 and 10 cm $H_2O$, and the experiment was repeated.

Air leak was computed from difference in inspiratory and expiratory tidal volumes, as read off the Servo Ventilator. Similar studies were also performed with a standard endotracheal tube of approximately same outside diameter, in which the cuff had been excised, or not inflated. The purpose of those studies was to assess air leak around a standard endotracheal tube of approximately same outside diameter at the level of the larynx, i.e. at the narrowest portion of the upper airways, and without relying upon the inflated cuff of the standard endotracheal tube for an airway seal.

In two separate studies, controlled ventilation in healthy anesthetized sheep, intubated with ultra-thin two-stage endotracheal tube of appropriate dimensions for the size of the sheep was conducted for 24 hours. After ventilation, the sheep were electively sacrificed. The trachea was carefully dissected, the changes in the trachea and the larynx were carefully noted.

The endotracheal tubes were found to be highly flexible, they could be acutely bent without kinking, and transmitted little torque on manual twisting. The endotracheal tubes of the present invention weighed approximately one third the weight of conventional PVC endotracheal tubes. Upon pressurization, there was some distension in the longitudinal direction, but not radially, i.e. while the tubes would lengthen, its diameter did not change. This lengthening was a function of wall thickness, and ranged from 0.05 mm/cm H₂O pressure for a 30 cm long endotracheal tube, with a wall thickness of 0.2 mm, to substantially less in endotracheal tubes with heavier walls.

While endotracheal tubes produced with stainless steel wire required moderate care to avoid damage, the endotracheal tubes reinforced with a shape memory alloy, e.g. Nitinol wire were uniquely different, as they could be occluded by forceful finger pressure, for example, with full and complete recovery upon release of pressure.

The increase in internal diameter in the new line of ultra-thin endotracheal tube was achieved solely on the basis of decrease in wall thickness, as seen in Table 1.

TABLE 1
CROSS-SECTIONAL DIMENSIONS OF STANDARD, ULTRA-THIN AND ULTRA-THIN TWO-STAGE ENDOTRACHEAL TUBES OF SAME LENGTH

| Standard ETT | | UT ETT | | UTTS ETT 1st stage | | UTTS ETT 2nd stage | | Equivalent to standard ETT mm 1.10 |
|---|---|---|---|---|---|---|---|---|
| ID mm | OD mm | ID mm | OD mm | ID mm | OD mm | ID mm | OD mm | |
| 2.5 | (3.6) | 3.2 | (3.6) | 3.2 | (3.6) | 5.0 | (5.4) | 4.2 |
| 2.8 | (4.0) | 3.6 | (4.0) | 3.6 | (4.0) | 5.0 | (5.4) | 4.7 |
| 3.6 | (5.1) | 4.6 | (5.1) | 4.6 | (5.1) | 5.8 | (6.2) | 5.5 |
| 3.8 | (5.4) | 4.9 | (5.4) | 4.9 | (5.4) | 6.4 | (6.8) | 5.7 |
| 5.2 | (6.8) | 6.35 | (6.6) | 6.35 | (6.8) | 7.9 | (8.3) | 7.6 |
| 5.7* | (7.6) | 7.2 | (7.6) | 7.2 | (7.6) | 9.2 | 9.7 | 8.0 |
| 6.2* | (8.3) | 7.9 | (8.3) | 7.9 | (8.3) | 9.5 | 10.0 | 9.0 |
| 7.5 | (10.0) | 9.5 | (10.0) | 9.5 | (10.0) | 11.0 | 11.4 | 10.8 |
| 8.0 | (10.7) | 10.3 | (10.7) | 10.3 | (10.7) | 12.5 | 12.9 | 11.7 |

*Dimension of imputed standard ET tube, with standard wall thickness.

Note:
In the ultra-thin two-stage endotracheal tube (UTTS ETT), the first stage was limited to 6 cm, with the remainder made up of the larger second stage.

TABLE 2

| | UTTS ETT | | | Standard Round ETT, without cuff I.D. 9.0 mm O.D. 12.0 mm PEEP, cm H₂O | | |
|---|---|---|---|---|---|---|
| | Horizontal axis I.D. 11.4 mm O.D. 11.9 mm PEEP cm H₂O | | | | | |
| | Vertical axis I.D. 14.2 mm O.D. 14.7 mm | | | | | |
| Peak airway pressure, cm H₂O | 0 | 5 | 10 | 0 | 5 | 10 |
| 15 | 0 | 0 | 0 | 80% | >90% | 100% |
| 20 | 0 | 0 | 0 | 82% | >90% | 100% |
| 25 | 0 | 0 | 0 | 82% | >90% | 100% |
| 30 | 0 | 6 | 0 | | | |
| 35 | 5 | 6 | 4 | | | |
| 40 | 10 | 12 | 8 | | | |
| 45 | 19 | 11 | 8 | | | |

By virtue of a smaller wall thickness, the internal diameter of a 7.5 mm conventional size endotracheal tube was increased to 9.5 mm in the ultra-thin endotracheal tube, the outside diameter being the same (10.0 mm) (Table 1). At a gas flows between 0.5 and 1 l/sec, this amounted to a 2-3 fold decrease in air flow resistance (FIG. 7). In the two-stage ultra-thin two-stage endotracheal tube, with the outside diameter of the tracheal portion of the ultra-thin two-stage endotracheal tube same as that of a standard 7.5 mm endotracheal tube, the pressure flow curve was equal to an imputed 10.8 mm standard endotracheal tube (Table 1, FIG. 6); at a gas flow from 0.5 to 1 l/sec, this amounted to a 4-5 fold decrease in air flow resistance.

When the ultra-thin two-stage endotracheal tube, with oval cross-section (lesser axis, outside diameter equivalent to a 8/7 mm conventional endotracheal tube; greater axis, outside diameter equivalent to a 10.5 mm conventional endotracheal tube) (FIG. 3), and attached "gills" at the level of the larynx was set in the proper position, there was no air leak at pressures up to 30 cm H₂O, at PEEP to 10 cm H₂O, in a 28 kg sheep; there was a minimum air leak starting at pressures 30-35 cm H₂O, as seen in Table 2.

In contrast, there was a prohibitive air leak over 80% at any PEEP level when using a conventional 9.0 mm endotracheal tube (outside diameter 12.0 mm), with the cuff removed, or not inflated. Following 24 hours of mechanical pulmonary ventilation with same ultra-thin two-stage endotracheal tube, there was no significant change in air leak from start of the studies.

Upon sacrifice, the trachea looked unremarkable, and healthy. The ultra-thin two-stage endotracheal tube was loosely positioned, the vocal cords looked unremarkable; a small pressure point could be seen in the glottis.

Although the present invention has been described with reference to particular means, materials and embodiments, from the foregoing description, one skilled in the art can ascertain the essential characteristics of the present invention and various changes and modification may be made to adapt the various uses and characteristics thereof without departing from the spirit and scope of the present invention as describe in the claims which follow.

What is claimed is:

1. A two-stage endotracheal tube which comprises:
   a first generally cylindrical portion having a first diameter which, when in use, is inserted into a subject's trachea, beyond the subject's larynx;
   a second generally cylindrical portion having a second diameter which, when in use, is positioned near the subject's mouth, said second diameter being greater than said first diameter;
   a tapered portion connecting said first and second generally cylindrical portions, a length of said second generally cylindrical portion adjacent said tapered portion being non-circularly shaped so as to be complementary to a subject's glottis; and a plurality of sealing means provided on said non-circular length of said second generally cylindrical portion, said plurality of seal means comprising thin, pliable gills which extend outward from said non-circular length of said second generally cylindrical portion, said gills having a thickness of about 0.02 to 0.075 mm, wherein the wall thickness of said first and second generally cylindrical portions and said tapered portion is between about 0.15 mm and 0.35 mm, and said gills have a diameter which is between 50-200% of a diameter of said non-circular portion of said second generally cylindrical portion.

2. A two-stage endotracheal tube according to claim 1, wherein said first and second generally cylindrical portions and said tapered portion each have a common, uniform wall thickness.

3. A two-stage endotracheal tube according to claim 1, wherein the wall thickness of said first and second generally cylindrical portions and said tapered portion is about 0.2 mm.

4. A two-stage endotracheal tube according to claim 1, wherein said non-circular portion comprises an oval shape.

5. A two-stage endotracheal tube according to claim 1, wherein said non-circular portion comprises an egg-shape.

6. A two-stage endotracheal tube according to claim 1, wherein said first and second generally cylindrical portions and said tapered portion are reinforced with a spring material.

7. A two-stage endotracheal tube according to claim 6, wherein said spring material comprises a shape memory alloy.

8. A two-stage endotracheal tube according to claim 7, wherein said shape memory material comprises a Ti-Ni alloy.

9. A two-stage endotracheal tube according to claim 6, wherein said first and second generally cylindrical portions and said tapered portion each have a common, uniform wall thickness of between about 0.15 mm and 0.35 mm.

10. A two-stage endotracheal tube according to claim 9, wherein the wall thickness of said first and second generally cylindrical portions and said tapered portion is about 0.2 mm.

11. An ultra-thin walled wire reinforced endotracheal tube comprising:

a generally cylindrical tubular wall of a predetermined length and a thickness of between about 0.15 mm and 0.35 mm;

a spring wire material incorporated within said generally cylindrical tubular wall, said spring wire material comprising a superelastic shape memory alloy; and a plurality of sealing means provided on a length of said generally cylindrical tubular wall, said plurality of seal means comprising thin, pliable gills which extend outward from said generally cylindrical tubular wall, said gills having a thickness of about 0.02 to 0.075 mm, and a diameter which is between 50-200% of a diameter of said length of said generally cylindrical tubular wall.

12. An ultra-thin walled wire reinforced endotracheal tube according to claim 11, wherein the thickness of said tubular wall is about 0.2 mm.

13. An ultra-thin walled wire reinforced endotracheal tube according to claim 11, wherein a plurality of sealing means are provided on an exterior surface of said tubular wall.

14. An ultra-thin walled wire reinforced endotracheal tube according to claim 13, wherein said plurality of sealing means comprises thin, pliable gills which extend outward from said non-circular length of said second generally cylindrical portion.

15. An ultra-thin walled wire reinforced endotracheal tube according to claim 11, wherein said shape memory material comprises a Ti-Ni alloy.

* * * * *